(12) United States Patent
Weigand

(10) Patent No.: US 9,543,107 B2
(45) Date of Patent: Jan. 10, 2017

(54) METHOD AND APPARATUS FOR GENERATING X-RAY RADIATION

(75) Inventor: Frank Weigand, Heidenheim (DE)

(73) Assignee: CARL ZEISS MEDITEC AG, Jena (DE)

( * ) Notice: Subject to any disclaimer, the term of this patent is extended or adjusted under 35 U.S.C. 154(b) by 178 days.

(21) Appl. No.: 14/239,188

(22) PCT Filed: Aug. 14, 2012

(86) PCT No.: PCT/EP2012/065863
§ 371 (c)(1),
(2), (4) Date: Feb. 17, 2014

(87) PCT Pub. No.: WO2013/024086
PCT Pub. Date: Feb. 21, 2014

(65) Prior Publication Data
US 2014/0233706 A1    Aug. 21, 2014

Related U.S. Application Data

(60) Provisional application No. 61/575,133, filed on Aug. 16, 2011.

(30) Foreign Application Priority Data

Aug. 16, 2011 (DE) .................. 10 2011 110 615

(51) Int. Cl.
*H01J 35/08* (2006.01)
*A61N 5/10* (2006.01)

(52) U.S. Cl.
CPC ............. *H01J 35/08* (2013.01); *A61N 5/1001* (2013.01); *A61N 2005/1022* (2013.01)

(58) Field of Classification Search
CPC ............. A61N 5/1001–5/1005; A61N 5/1014; A61N 5/1022; A61N 5/103; A61N 5/1031; A61N 5/1032; A61N 5/1034; A61N 5/1035; A61N 2005/1003–2005/1005; A61N 2005/1022; A61N 2005/1032–2005/1034; H05G 1/02; H05G 1/30; H05G 1/32; H05G 1/42; H01J 35/08

See application file for complete search history.

(56) References Cited

U.S. PATENT DOCUMENTS

| 5,647,663 A | 7/1997 | Holmes |
| 6,421,416 B1 | 7/2002 | Sliski et al. |

(Continued)

FOREIGN PATENT DOCUMENTS

| DE | 102005018330 A1 | 10/2006 |
| DE | 102006043551 A1 | 3/2008 |

(Continued)

OTHER PUBLICATIONS

Birch et al., "A contact x-ray therapy unit for intracavitary irradiation," Physics in Medicine and Biology, 35 (2):275-280 (1990).

(Continued)

*Primary Examiner* — David E Smith
(74) *Attorney, Agent, or Firm* — Kriegsman & Kriegsman

(57) ABSTRACT

The present invention relates in particular to methods and apparatuses for generating and/or providing X-ray radiation with specific radiation characteristics, in particular with a specific radiation dose rate curve (10). In order to provide simple and cost efficient solution, it is provided according to the invention, that the X-ray radiation is generated and/or provided, by composing and/or adapting the X-ray radiation with the specific radiation characteristics, in particular with the specific radiation dose rate curve (10), proportionally from a first specification X-ray radiation with a defined first radiation characteristics, in particular with a predetermined first radiation dose rate curve (11) and a second specification X-ray radiation, which is different from the first specification (Continued)

X-ray radiation, with defined second radiation characteristics, in particular with a predetermined second radiation dose rate curve (12).

20 Claims, 4 Drawing Sheets

(56) References Cited

U.S. PATENT DOCUMENTS

| | | | | |
|---|---|---|---|---|
| 6,810,109 | B2* | 10/2004 | Chornenky | H05G 1/46 |
| | | | | 378/108 |
| 8,724,775 | B2 | 5/2014 | Kleinwaechter et al. | |
| 2008/0253532 | A1* | 10/2008 | Hess | A61B 6/542 |
| | | | | 378/108 |
| 2011/0060602 | A1* | 3/2011 | Grudzinski | G06Q 50/22 |
| | | | | 705/2 |
| 2014/0328467 | A1 | 11/2014 | Weigand | |

FOREIGN PATENT DOCUMENTS

| | | |
|---|---|---|
| DE | 102009014693 A1 | 12/2010 |
| DE | 102009019199 A1 | 1/2011 |
| DE | 102010036046 A1 | 3/2011 |
| FR | 2534066 A1 | 4/1984 |
| GB | 2049320 A * 12/1980 | ............... H05G 1/18 |
| WO | 9504501 A1 | 2/1995 |
| WO | 03007669 A1 | 1/2003 |
| WO | 2009132799 A2 | 11/2009 |

OTHER PUBLICATIONS

Fletcher et al., "Note; An assessment for GafChromic film for measuring 50 kV and 100 kV percentage depth dose curves," Physics in Medicine and Biology, 53(11): N209-18 (2008).

Eaton et al, "Note; Dosimetry measurements with an intra-operative x-ray device," Physics in Medicine and Biology, 55(12): N359-69 (2010).

International Preliminary Report on Patentability from PCT/EP2012/065863 dated Feb. 27, 2014.

* cited by examiner

METHOD AND APPARATUS FOR GENERATING X-RAY RADIATION

The present invention relates to a method and an apparatus for generating and/or providing a specific radiation dose rate curve for X-ray radiation for irradiating a substrate. Furthermore, the present invention relates to an apparatus and a method for generating and/or providing of X-ray radiation with specific radiation characteristics, in particular with a specific radiation dose rate curve.

Apparatuses and methods of this kind are for example used in the field of irradiation therapy by means of irradiation devices. Intraoperative irradiation is nowadays often carried out with modern irradiation devices, which allow for the radiation to be brought immediately to the location of irradiation, for example into a tumor or to a tumor bed.

The X-ray radiation, which is required for a respective irradiation, is usually generated in or by means of an X-ray radiation source. In particular, the X-ray radiation source is a component of the irradiation device. The operating principle of known X-ray radiation sources, for example for intraoperative irradiation, is in particular based on the fact, that electrons are being generated in an electron source and are being emitted as an electron beam. The electron beam is accelerated in an acceleration stage by means of an acceleration voltage, which in particular is high voltage. The thus generated and accelerated electron beam is directed onto a target, which may for example be made of gold. The target may for example be located in the tip of an applicator. Upon impinging of the electron beam on the target, the X-ray radiation is being generated, which is then being emitted from the target in the shape of a resulting X-ray radiation field with specific radiation characteristics. Such an irradiation device is for example described in WO 2009/132799 A2.

If the substrate, which is to be irradiated, is tissue, the required radiation dose, which is supposed to arrive in a defined distance to the X-ray radiation source on the tissue, which is to be irradiated, has to be determined. By means of the radiation dose rate, which is a rate function of the irradiation device and which decreases with increasing distance from the X-ray radiation source, the required irradiation time for the tissue, which is to be irradiated, can be determined, such that the required radiation dose arrives on the tissue or is being delivered to or into the tissue. The irradiation is carried out for the determined irradiation time by using the determined or selected radiation dose rate.

As the X-ray radiation, which is emitted from the X-ray radiation source, penetrates through the substrate, for example the tissue, also other locations than the location, where the defined radiation dose is to be applied, are being irradiated. As the X-ray radiation source is normally placed onto the surface of a substrate or within a substrate, and the X-ray radiation propagates from the X-ray radiation source, the radiation dose rate decreases with increasing distance from the X-ray radiation source. This means, that immediately at the X-ray radiation source a higher radiation dose rate value is available, than in a distance there from.

The capability of an X-ray radiation source of providing such radiation dose rate values is for example described by the so called radiation dose rate curve. With these curves, the radiation dose rate values which can be provided by the X-ray radiation source for different distances from the X-ray radiation source, for example from the isocentre of the X-ray radiation source, are determined. The connection between the points of the radiation dose rate values for different distances from the X-ray radiation source results in the radiation dose rate curve. By means of such radiation dose rate curve, the user can determine, which radiation dose is applied at which location of the substrate.

The course, for example the slope, of such a radiation dose rate curve is among other factors dependent from the applied acceleration voltage.

The radiation characteristics of X-ray radiation sources, which, for example, are the emission characteristics of the generated X-ray radiation from the target, are, however, even at identical operation voltages, always different, since the X-ray radiation sources are never completely identically designed due to unavoidable manufacturing tolerances and differences in material. For carrying out an irradiation, for example the treatment of a patient, the radiation characteristics of the exact X-ray radiation source, which is used, however, have to be known. Therefore, X-ray radiation sources are always being calibrated, which may also be referred to as measured or surveyed, before being put to use for the first time, in order to determine the radiation characteristics of the specific X-ray radiation source, in particular their radiation dose rate curve(s). Such measurements are, however, very complex or cumbersome. Therefore, they are only carried out at specific acceleration voltages. Generally, the X-ray radiation source is then also only operated at those acceleration voltages, for which a calibration has been carried out, since the exact radiation characteristics of the X-ray radiation source are not known for other acceleration voltages.

Thereby, the measuring of an X-ray radiation source, in particular for different acceleration voltages is a time-consuming and costly means.

Starting from the cited state of the art, the present invention is based on the problem, to further develop the initially mentioned apparatuses and the initially mentioned methods, such that the above mentioned problems can be avoided.

According to the present invention, this problem is solved by the methods with the features according to independent claims 1, 2 and 3 as well as by the apparatuses with the features according to independent claims 9, 10 and 11. Further features and details of the invention become clear from the dependent claims, the description as well as from the figures. Therein, features and details, which are described in connection with one aspect of the apparatus according to the invention, also apply in connection with the respective other aspects of the apparatus according to the invention. Features and details, which are described in connection with one aspect of the method according to the invention, also apply in connection with the respective other aspects of the method according to the invention. Features and details, which are described in connection with the apparatus(es) according to the invention, apply with respect to their disclosure in their entirety also in connection with the method(s) according to the invention, so that statements made with respect to the apparatus(es) also apply to their full extent to the method(s) and vice versa.

An underlying concept of the present invention is that the radiation characteristics of a generated or provided X-ray radiation is varied, which according to the present invention is in particular being carried out over time.

The present invention lies in particular within the field of irradiation of substrates, preferably in connection with irradiation of tissue, in particular of tumors and the like. Therein, it is in particular provided that the irradiation of a substrate is performed in such a way, that radiation is emitted to the substrate and arrives on the substrate and/or penetrates into the substrate. Radiation, in the very general sense, is the propagation of particles or waves, wherein in particular energy and/or impulse is transported. According to the present invention the radiation is preferably X-ray radiation.

The radiation is generated by a radiation source. The radiation source generally serves for being able to generate, emit and/or provide a radiation dose. A radiation dose is in particular the absorbed or absorbable amount of, in particular of ionized, radiation in a substrate, for example in a tissue. The radiation dose, which is absorbed per time unit and per mass unit is referred to as radiation dose rate. At a specific acceleration voltage a radiation source has in particular a specific radiation dose rate. A radiation dose rate curve is in particular the course of the radiation dose in the depth. The origin is the radiation source and in particular the isocentre thereof. The isocentre of irradiation devices is in particular the centre point of the smallest ball, through which the central ray at all rotation angles passes through. In general, it can be said that the isocentre is the centre from which the radiation starts or origins.

The radiation source may, for example, be an X-ray radiation source. The generated radiation then is X-ray radiation.

According to the invention, a specific radiation dose rate curve is generated and/or provided for X-ray radiation for irradiating a substrate, in particular a tissue. In a different embodiment, X-ray radiation with specific radiation characteristics, for example with specific emission characteristics, as described above, in particular with a specific radiation dose rate curve, is generated and/or provided.

Such a radiation dose rate curve is in particular the course of the radiation dose rate, which is available for an irradiation, in the depth. The radiation dose rate is in particular the energy of the radiation, which is emitted from the X-ray radiation source, at a defined location, for example in a specific distance from the X-ray radiation source, with respect to the mass unit of the substrate, in particular of tissue material, and with respect to a time unit. The origin therein is the X-ray radiation source and in particular the isocentre of the X-ray radiation source. The radiation dose rate curve has a maximum value at the location of the radiation source, in particular at the location of the isocentre of the X-ray radiation source. With increasing distance there from, the radiation dose rate curve drops. This may occur, for example, due to absorption of the radiation by the irradiated substrate as well as due to the spatial distribution with increasing distance from the X-ray radiation source.

Such a radiation dose rate curve is preferably a so called depth dose rate curve, in particular a depth dose rate curve in water.

For irradiation of a substrate, in particular for the treatment of a patient with irradiation, in general the depth dose rate curve in water with the physical unit Gray per minute [Gy/min], which is also referred to as DDC, is an important parameter of the X-ray radiation source. The depth dose rate curve in water is a function of the water depth, wherein the origin (0 mm) is the X-ray radiation source and in particular the isocentre of the X-ray radiation source. The depth dose rate curve in water is measured during the production and also during re-calibration of each X-ray radiation source and is typical for this X-ray radiation source.

As the X-ray radiation source is approximately an X-ray point source, the course of the depth dose rate curve in water is determined on one hand by the inverse square law ($f(x) \sim 1/x^2$) and on the other hand by the absorption of the generated X-ray radiation in water ($f(x) \sim I_0 * \exp(-\mu_w * x)$).

As the X-ray radiation, in this case $I_0$, of an X-ray radiation source, in contrast to, for example, radioactive sources, is composed of a complex spectrum, $I_0$ is a function of the energy E. As the absorption coefficient of water ($\mu_w$) is also a function of the energy E, the absorption is strongly dependent from the spectrum of the respective X-ray radiation source.

The spectrum of an X-ray radiation source is composed of the characteristic spectrum by the used materials and the X-ray braking spectrum, in particular by the acceleration voltage of the electrons.

With equipment, as used today, the user can choose at an irradiation device between three different acceleration voltages U. The acceleration voltages U are for example thirty kilovolts (30 kV), forty kilovolts (40 kV) and fifty kilovolts (50 kV), wherein the acceleration voltage is, however, fixed for the duration of the treatment and cannot be changed anymore.

With the present invention this approach can be departed from, as will be described later in detail. The acceleration voltage can now be changed during the irradiation treatment.

As the X-ray radiation sources in general are similar in their design, the X-ray spectra do not differ significantly at the same acceleration voltage and the depth dose rate curves in water, the DDC, are approximately identical with respect to their course. This course is recognizable by a decrease of the function with increasing water depth.

The absolute height of the depth dose rate curve in water (DDC) can, however, vary, which can be compensated for by different irradiation times, if the same dose is to be applied in a specific depth with different X-ray radiation sources.

It may, however, frequently be of crucial importance, that the course of the depth dose rate curve in water (DDC), that means the decrease of the emitted radiation dose with increasing water depth, is similar or comparable, for all X-ray radiation sources, which are used.

As already indicated above, with the current solutions, one is fixed to a set selection from a limited number of different acceleration voltages for a desired irradiation. This is caused by the cost and time-consuming calibration of the X-ray radiation source at the selectable acceleration voltages. Therefore, one can only select from the respective courses of the depth dose rate curves in water (DDC) at these specific acceleration voltages. The present invention allows for a deviation from these restrictions.

It also becomes possible with the present invention, that X-ray radiation sources can be put to use, with which many different depth dose rate curves in water (DDC) can be generated.

According to the first aspect of the invention, a method for generating and/or providing a specific radiation dose rate curve for an X-ray radiation for irradiation of a substrate is provided. The method is characterized in that the specific radiation dose rate curve is generated and/or provided, by selecting at least two predetermined radiation dose rate curves, which are different from the specific radiation dose rate curve, which is to be generated and/or provided, and by composing and/or adapting the specific radiation dose rate curve proportionally from the at least two predetermined radiation dose rate curves. The proportional composing and/or adaption can also be referred to as a proportionate or pro-rata composing and/or adaption.

According to this first aspect, it is intended to generate and/or provide a specific radiation dose rate curve for X-ray radiation for irradiating a substrate.

The specific radiation dose rate curve is in particular such a radiation dose rate curve, which is not available so far. This radiation dose rate curve is rather to be generated and/or provided by the method according to the invention. The term "generated" is in particular understood such, that such a radiation dose rate curve is created. The term "provided" is in particular understood such, that the radiation dose rate curve is delivered for an application. The radiation dose rate curve may be such a radiation dose rate curve, which has been described further above.

This specific radiation dose rate curve is generated and/or provided in a special way. Starting point for this are at least two predetermined radiation dose rate curves, which are already available or known. These predetermined radiation dose rate curves may also be referred to as specification radiation dose rate curves. The predetermined radiation dose rate curves differ from one another. These radiation dose rate curves may, for example, be generated by a calibration or measurement as described above. It may, for example, be provided, that the two predetermined radiation dose rate curves are such radiation dose rate curve, which have been measured at different acceleration voltages.

In the simplest case, two of such predetermined radiation dose rate curves are used. Of course, according to the invention also more than two of such predetermined radiation dose rate curves may be used.

According to the invention it is provided, that the predetermined radiation dose rate curves are different from the specific radiation dose rate curve, which is to be generated and/or provided. Preferably, it is provided, that a predetermined radiation dose rate curve is or forms an upper limit and that another predetermined radiation dose rate curve is or forms a lower limit. The specific radiation dose rate curve, which is to be generated and/or provided, according to the present invention, preferably lies between the predetermined radiation dose rate curves. That means in particular, that the specific radiation dose rate curve is generated in a way that the specific radiation dose rate curve or its course lays between the predetermined radiation dose rate curves.

According to the invention at least two such predetermined radiation dose rate curves are chosen or selected. The radiation dose rate curve, which is to be generated and/or provided, is then created or generated, by composing and/or adapting the specific radiation dose rate curve proportionally from the at least two predetermined radiation dose rate curves.

According to a second aspect of the invention, a method for generating and/or providing of X-ray radiation with specific radiation characteristics, in particular with a specific radiation dose rate curve, is provided. The method is characterized in that the X-ray radiation is generated and/or provided by composing and/or adapting the X-ray radiation with the specific radiation characteristics, in particular with the specific radiation dose rate curve, proportionally from a first specification X-ray radiation with defined first radiation characteristics, in particular with a first predetermined radiation dose rate curve—which, in particular, is a defined first radiation dose rate curve—, and a second specification X-ray radiation with defined second radiation characteristics, in particular with a predetermined second radiation dose rate curve-which, in particular, is a defined second radiation dose rate curve —, wherein the second specification X-ray radiation differs from the first specification X-ray radiation.

With the method according to the second aspect of the invention, an X-ray radiation is generated and/or provided. This X-ray radiation is supposed to have specific radiation characteristics, which may be emission characteristics, which are described further above. In particular, X-ray radiation with a specific radiation dose rate curve is to be generated and/or provided. The method according to the second aspect is thus a preferred embodiment of the generally mentioned context of the method according to the first aspect, so that the respective explanations from above are referred to here and are incorporated by reference at this point.

According to a third aspect of the invention, a method for generating and/or providing of X-ray radiation with specific radiation characteristics, in particular with a specific radiation dose rate curve, is provided, which is, in particular, an advantageous embodiment of the afore mentioned method according to the second aspect of the invention, so that reference is made to the respective description above and is incorporated by reference at this point. The method according to the third aspect of the invention describes a more concrete embodiment of the method by using a specific X-ray radiation source.

With this method by means of an electron source an electron beam is generated. The electron beam is accelerated by means of an acceleration voltage and is directed towards a target. An X-ray radiation is generated by electrons of the electron beam impinging on the target.

The method is characterized in that the X-ray radiation is generated and/or provided by composing and/or adapting the X-ray radiation with the specific radiation characteristics proportionally from a first specification X-ray radiation with defined first radiation characteristics, which are associated to a first acceleration voltage, and a second specification X-ray radiation with defined second radiation characteristics, which are associated to a second acceleration voltage, by proportionally alternately accelerating the electron beam with the first acceleration voltage and with the second acceleration voltage. Herein the second specification X-ray radiation differs from the first specification X-ray radiation.

With this embodiment of the method an apparatus for generating X-ray radiation is provided. This apparatus has an X-ray radiation source or is designed as an X-ray radiation source.

Preferably, the methods according to the three above mentioned aspects of the invention are carried out with corresponding apparatuses according to the further aspects of the invention, which are described further below, so that at this point with regard to the disclosure reference is made to the respective explanations with respect to the apparatuses according to the invention made further below and these explanations are incorporated by reference at this point.

The invention is preferably directed to the generating of a low-energy and/or soft X-ray radiation. The apparatus is preferably part of an irradiation device.

A basic feature of the present invention is now in particular, that an X-ray radiation source, which is in particular designed for the usage at two or more acceleration voltages, is operated in such a way, that thereby also radiation dose rate curves can be provided, which lie between a first radiation dose rate curve, which is in particular associated to a first acceleration voltage, and a second radiation dose rate curve, which is in particular associated to a second acceleration voltage. For this purpose, a respective apparatus, in particular according to a given or fixed plan, is alternately operated with the first acceleration voltage and the second accelerating voltage, and optionally also with further acceleration voltages.

In particular, with the invention the adaption of a radiation dose rate curve can be carried out by changing the acceleration voltage.

In comparison to the known solutions from the prior art, the present invention allows for a deviation from a fixed acceleration voltage during the operation, for example during a treatment.

Radiation dose rate curves, in particular depth dose rate curves in water (DDC) only have to be measured for few, in the minimum case for two, different acceleration voltages, for example during the manufacturing or recalibration of an X-ray radiation source. The generating and/or providing of a radiation dose rate curve, which differs there from, can be generated there from, for example by a calculation and/or determination of the desired radiation dose rate curve by adaption of the measured radiation dose rate curves, in particular by means of a computing appliance, a software or the like. The computing appliance may also be referred to as a computing unit or computing means.

In general all appliances of the apparatus(es) of the present invention, which have or will be described, may each be referred to as a unit or as means.

The adaption is, in particular, carried out by determining the proportional relation of the predetermined radiation dose rate curves and the irradiation times resulting there from. A subsequent treatment can be carried out by proportional irradiation with the calculated different acceleration voltages.

By measuring of only a few radiation dose rate curves, which are in particular predetermined radiation dose rate curves, and a simulation of further radiation dose rate curves, which are in particular predetermined radiation dose rate curves, from these measures curves, a considerable cost reduction may be achieved.

This shall be demonstrated by means of an example. For example, during the manufacturing of an X-ray radiation source, radiation dose rate curves, in particular depth dose rate curves in water (DDC) for acceleration voltages of 30 kV and 50 kV have been measured or surveyed. These are, in particular, the predetermined radiation dose rate curves. From these radiation dose rate curves one can now produce a radiation dose rate curve, in particular a depth dose rate curve in water (DDC), for an acceleration voltage, which lies there between, of 40 kV, namely from specific portions 30 kV and specific portions 50 kV. This radiation dose rate curve is in particular the specific radiation dose rate curve. It may for example be provided that one can produce or generate the radiation dose rate curve with 40 kV by means of 0.69 portions radiation dose rate curve with 50 kV and 0.31 portions radiation dose rate curve with 30 kV.

Preferably, the specific radiation dose rate curve can be determined and/or calculated with respect to the first aspect of the invention from the predetermined radiation dose rate curves. With respect to the second and third aspect of the invention, the X-ray radiation with the specific radiation characteristics, in particular with the specific radiation dose rate curve, can be determined and/or calculated from the specification X-ray radiations with the defined radiation characteristics, in particular the specific radiation dose rate curves. For this purpose, in particular a computing appliance may be provided, wherein the calculation and/or determination is carried out. For the calculation a specific software and/or computer program product may be employed. The advantages of this approach have already been described further above. In particular, the specific radiation dose rate curve and/or the X-ray radiation with specific radiation characteristics can be simulated from the measured, predetermined values. That means, that only a few measurements actually have to be carried out, which leads to a simplification of the method and to a cost reduction.

In a further embodiment with respect to the first aspect of the invention, the specific radiation dose rate curve can be determined and/or calculated from specification values for the specific radiation dose rate curve. With respect to the second and third aspect of the invention, the X-ray radiation with specific radiation characteristics, in particular with a specific radiation dose rate curve is determined and/or calculated from specification values for an X-ray radiation with the specific radiation characteristics, in particular with a specific radiation dose rate curve. That means that from the user side, for specific application purposes and the like, respective specification can be made. For example, it may be achieved that a user wants to irradiate with specific radiation dose rate curves and/or X-ray radiation with specific radiation characteristics, which have been generated by him. With the mentioned embodiment, the best adaption or approximation from given radiation dose rate curves and/or specification X-ray radiation may be performed, for example, by respective calculations in a generating appliance, which has been provided for that purpose. The generating appliance may also be referred to as generating unit or generating means. Such a generating appliance will be described further below in connection with the apparatuses according to the invention in further detail. The generating appliance may be part of a computing appliance or may be a computing appliance. The adaption parameters, which are used for this purpose, determine the proportional ratio of the specifications and thereby the individual irradiation times.

Preferably, the generated and/or provided specific radiation dose rate curve or parameters and/or values of the generated and/or provided X-ray radiation with specific radiation characteristics, in particular with the specific radiation dose rate curve, are stored in a storage appliance. Such a storage appliance, which may also be referred to as storage unit or storage means, will also be described further below in connection with the apparatuses of the invention in more detail. Thereby, the stored data is available for further applications. Therein, it is preferably provided, that a respective apparatus for generating and/or providing of X-ray radiation, in particular a computing appliance of such an apparatus, has such a storage appliance or can at least access such a storage appliance via an interface.

In a further embodiment, it is preferably provided, that the specific radiation dose rate curve according to the first aspect of the invention is composed and/or adapted in a subsequent manner with regard to or in a temporal change from the at least two predetermined radiation dose rate curves, or that the X-ray radiation with the specific radiation characteristics, in particular with the specific radiation dose rate curve, according to the second aspect of the invention is composed and/or adapted in a subsequent manner with regard to or in a temporal change from the first specification X-ray radiation and the second specification X-ray radiation or that the electron beam according to the third aspect of the invention is accelerated in a subsequent manner with regard to or in a temporal change with the first acceleration voltage and the second acceleration voltage. This can for example be embodied by means of a time switch appliance, which may also be referred to as a time switch unit or time switch means. Such a time switch appliance will also be explained further below in connection with the apparatuses according to the invention in more detail.

This means in particular, that an irradiation, which is based on the generated and/or provided results, can either be carried out in a subsequent manner or by change. In either case, it is ensured, that after the total duration of the irradiation, the respectively calculated individual irradiation times have been carried out. For example, in a preferred embodiment, a repeated change of the acceleration voltage per second or minute can be carried out. Referring back to the above mentioned example, it may for example be provided, that a repeated change of the acceleration voltage is performed during the irradiation, for example as 0.69*1 minute at 50 kV, then 0.31*1 minute at 30 kV, and this routine is carried out for example 20 times. In a different embodiment, it is also possible to irradiate for example also in a subsequent manner proportionately with different acceleration voltages, for example 0.69*20 minutes at 50 kV, then 0.31*20 minutes at 30 kV.

It is preferably provided, that the specific radiation rate dose curve according to the first aspect of the invention is composed and/or adapted by means of linear combination from the at least two predetermined radiation rate dose curves, or that the X-ray radiation with the specific radiation characteristics, in particular with the specific radiation dose rate curve, according to the second or third aspect of the invention is composed and/or adapted by means of linear combination from the first specification X-ray radiation and the second specification X-ray radiation. The linear combination as such is known as a mathematical method. A linear combination is in particular a vector which is formed of the sum of several other vectors. A measuring of all radiation rate dose curves for all acceleration voltages is thus not necessary any longer. The missing radiation rate dose curves may rather be formed by a few measured radiation rate dose curves by means of linear combination of the measured radiation rate dose curves.

In the further course of the description, different apparatuses are described, which in particular are suitable for performing the above described methods. With regard to the apparatuses reference is therefore made with respect to the disclosure to the above mentioned description of the methods according to the invention and its content is incorporated by reference and vice versa.

According to a fourth aspect of the present invention, which in particular corresponds to the above mentioned first aspect of the invention, an apparatus for generating and/or providing a specific radiation rate dose curve for an X-ray radiation for irradiation of a substrate is provided. This apparatus is characterized in that the apparatus has a selection appliance for selecting at least two predetermined radiation dose rate curves, which are different from the specific radiation dose rate curve, which is to be generated and/or provided, and that the apparatus has an appliance for proportionally composing and/or adapting the specific radiation dose rate curve from the at least two predetermined radiation dose rate curves. The selection appliance may also be referred to as a selection unit or selection means. The appliance for composing and/or adapting may also be referred to as a unit or means for composing and/or adapting. With respect to the embodiment and functional concept of the apparatus, reference is also made to the explanations provided in the above description with respect to the method according to the invention and the content thereof is incorporated by reference at this point.

According to a fifth aspect of the present invention, which in particular corresponds to the above described second aspect of the invention, an apparatus for generating and/or providing of X-ray radiation with specific radiation characteristics, in particular with a specific radiation rate dose curve, is provided. The apparatus is characterized in that the apparatus has an appliance for generating and/or providing a first specification X-ray radiation with defined first radiation characteristics, in particular with a predetermined first radiation dose rate curve, and a second specification X-ray radiation with defined second radiation characteristics, in particular with a predetermined second radiation dose rate curve, wherein the first specification X-ray radiation is different from the second specification X-ray radiation, and that the apparatus has an appliance for proportionally composing and/or adjusting the X-ray radiation with the specific radiation characteristics, in particular with the specific radiation dose rate curve, from the first specification X-ray radiation and the second specification X-ray radiation. With respect to the embodiment and functional concept of the apparatus reference is also made to the explanations provided in the above description with respect to the method according to the invention and the content thereof is incorporated by reference at this point.

According to a sixth aspect of the present invention, which in particular corresponds to the above described third aspect of the invention, an apparatus for generating and/or providing of X-ray radiation with specific radiation characteristics, in particular an apparatus as described before, is provided. The apparatus is characterized by an electron source for generating an electron beam, a target for generating X-ray radiation by electrons from the electron beam impinging on the target, an acceleration appliance for accelerating the electrons of the electron beam by means of an applied acceleration voltage, an appliance for generating and/or providing a first specification X-ray radiation with defined first radiation characteristics, in particular with a predetermined first radiation dose rate curve, which is associated to a first acceleration voltage, and a second specification X-ray radiation, which is different from the first X-ray radiation, with defined second radiation characteristics, in particular with a predetermined second radiation dose rate curve, which is associated to a second acceleration voltage, as well as an appliance for proportionally composing and/or adapting the X-ray radiation with the specific radiation characteristics, in particular with the specific radiation dose rate curve, from the first specification X-ray radiation and the second specification X-ray radiation, wherein the appliance is designed for influencing the accelerating appliance, such that the electron beam is accelerated or can be accelerated proportionally alternately with the first acceleration voltage and the second acceleration voltage. With respect to the embodiment and functional concept of the apparatus reference is also made to the explanations provided in the above description with respect to the method according to the invention and the content thereof is incorporated by reference at this point.

The above mentioned apparatus firstly has an electron source. By means of the electron source, electrons are generated, which in particular are emitted as an electron beam. The electron source thus serves in particular for generating an electron beam. Furthermore, the apparatus has a target, wherein the target may for example be made of gold. The target serves for the actual generating of the X-ray radiation. The electrons which are generated by the electron source impinge on the target as an electron beam. By the electrons of the electron beam, which impinge on the target, the X-ray radiation is generated, which is emitted from the target.

The method(s) according to the invention as well as the apparatus(es) according the invention may in particular be used in the field of intraoperative irradiation. Herein, the X-ray radiation, in particular of short range, is being used, which can be brought immediately in the or to the irradiation location, for example a tumor or to the tumor bed. In an X-ray radiation source, which is used for this purpose, electrons are generated in an electron source. The electrons are accelerated as an electron beam with an acceleration voltage towards the target, which is for example made of gold. There, the in particular low energy X-ray radiation is generated, which is in particular isotropically emitted and penetrates into the tissue, which is to be irradiated.

X-ray probes, which have a tip made of beryllium, are often being used for such an irradiation therapy. Beryllium is material which is almost transparent for X-ray radiation. The X-ray probe is preferably designed as an evacuated electron beam tube. In this electron beam tube, a beam of electrons is generated by means of the electron source, which is then being accelerated by means of an acceleration voltage. The electron beam is directed towards the target. On the target, the electrons are abruptly slowed down and X-ray radiation is being generated.

Such an apparatus preferably has an acceleration appliance for accelerating the electrons by means of an acceleration voltage, which may also be referred to as electron accelerator. The acceleration appliance or accelerator may also be referred to as an acceleration unit or acceleration means. The acceleration of the electrons is effected in particular by means of high voltage, which is applied at the acceleration appliance. Preferably, the apparatus is designed for actuating the acceleration appliance. This means for example, that the apparatus is designed to handle the acceleration appliance in such a way that by means of the acceleration appliance the desired acceleration voltage is provided. The actuating of the acceleration appliance is preferably carried out in such a way that by actuating the acceleration appliance, the acceleration voltage for accelerating the electron beam, which impinges on the target, is varied or may be varied with respect to the acceleration voltage values, in particular during the operation of the apparatus. Preferably it is provided, that it may be switched between different acceleration voltages, via the acceleration appliance. The acceleration appliance is thus designed for a selective switching between at least two different acceleration voltages. For example, the acceleration appliance may be part of a computing appliance or may be controlled by a computing appliance.

Due to this preferred embodiment, in particular a deviation from a fixed acceleration voltage becomes possible, so that in particular different radiation rate dose curves can be generated. That means that the apparatus is preferably designed to handle the acceleration appliance in a way, that—via this acceleration appliance—the electron beam can be accelerated with different acceleration voltages to the target.

The present invention is not limited to certain acceleration voltages. Preferably, an acceleration voltage between 0 and 150 kV is applied. For irradiation of tissue preferably an acceleration voltage between 10 and 100 kV is applied.

Preferably, the apparatus has a computing appliance for determining and/or calculating the specific radiation rate dose curve from the predetermined radiation rate dose curves or for determining and/or calculating the X-ray radiation with the specific radiation characteristics, in particular with the specific radiation rate dose curve from the specification X-ray radiation with the defined radiation characteristics, in particular the specific radiation rate dose curves.

Alternatively or additionally, the apparatus preferably has a storage appliance for storing the specific radiation rate dose curve or parameters and/or values of the X-ray radiation with the specific radiation characteristics, in particular with the specific radiation rate dose curve.

In a further embodiment, the apparatus may have an interface for receiving and/or an input appliance for input of specification values for a specific radiation dose rate curve, or of specification values for the X-ray radiation with specific radiation characteristics, in particular with the specific radiation dose rate curve. The specification values are transmitted via the interface—in particular from externally—to the apparatus. The input appliance, which may also be referred to as an input unit or input means, may for example be a key board, a touch panel, a reader for reading in data and the like.

In a further embodiment, the apparatus may have a generating appliance for generating a specific radiation dose rate curve or an X-ray radiation with specific radiation characteristics, in particular with a specific radiation dose rate curve from specification values. With respect to the functional concept of such appliances reference is also made to the explanations provided in the above description with respect to the method according to the invention and the content thereof is incorporated by reference at this point.

Preferably, the apparatus has a time switch appliance, which is designed such that the specific radiation dose rate curve is or can be composed and/or adapted in a subsequent manner with regard to time or in a temporal change from the at least two predetermined radiation dose rate curves or that the X-ray radiation with the specific radiation characteristics, in particular with the specific radiation dose rate curve, is or can be composed and/or adapted in a subsequent manner with regard to time or in a temporal change from the first specification X-ray radiation and the second specification X-ray radiation, or that the electron beam is or can be accelerated in a subsequent manner with regard to time or in a temporal change with the first acceleration voltage and the second acceleration voltage. With respect to functional concept of such a time switching appliances reference is also made to the explanations provided in the above description with respect to the method according to the invention and the content thereof is incorporated by reference at this point.

The apparatuses according to the invention have in particular means for carrying out the methods according to the invention, which have been described above, so that all explanations and statements which have been made with respect to the methods with respect to its disclosure also apply with respect to the apparatuses, and vice versa.

The invention will now be explained in more detail with respect to exemplary embodiments with reference to the enclosed drawings, wherein.

Figure 1:
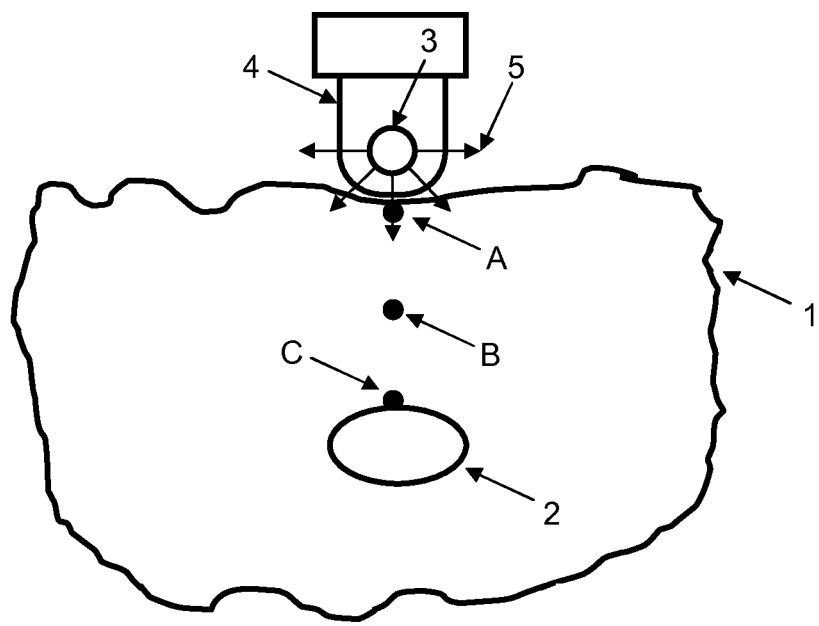
FIG. 1 shows a schematic depiction of an irradiation of a substrate by means of an irradiation device.

In FIG. 1 a schematic depiction of an irradiation of a substrate 1 by means of an irradiation device is shown. In general, during irradiation a radiation source 3, which may for example be introduced or placed in an applicator 4, is placed on the surface of a substrate 1, which is to be irradiated. The goal of the irradiation may be that a location 2 within the substrate 2, which may be a tumor, is irradiated.

The user, for example a medical doctor, determines or sets the radiation dose, which is to be emitted to the or is to arrive at or is to be absorbed by the location 2, which is to be irradiated, for the irradiation. This can, for example, be preformed by the user setting the radiation dose, which may also be referred to as radiation dose value, which is to be applied at a specific point, for example point C, of the location 2, which is to be irradiated.

The radiation dose is then applied by the radiation dose rate which is emitted from the radiation source 3 and the irradiation time. The required radiation dose, that means the required radiation dose value, at point C is applied by the radiation dose rate value, which is present at point C and the irradiation time. As the radiation source 3, however, emits in all spatial directions, which is indicated by arrows 5, also radiation does rate values are applied at points A and B within the substrate 1.

Point A in FIG. 1 is immediately at the surface of the substrate 1, that means at the location, where the radiation source 3 is placed. Point C is within the substrate 1, or more specifically, is exactly at the location 2, which is to be irradiated, that means is in a distance to the surface of substrate 1. Point B is also within the substrate 1, but not as deep as point C. Point B is between point A and point B.

Since the radiation during irradiation of the location 2, which is to be irradiated, starting form the radiation source 3 propagates in all spatial directions, different radiation dose rate values are present at points A, B and C during the irradiation. These occur, as a radiation dose rate is provided by the radiation source 3, which decreases with increasing distance from the isocentre of the radiation source 3.

Due to the irradiation time a specific radiation dose occurs at points A, B and C, since the radiation dose corresponds to the product of radiation dose rate or radiation does rate value and irradiation time.

The radiation dose rate value and thus also the radiation dose, which are present at point A, are larger or higher than the radiation dose rate value and the radiation dose, which are present in points B and C. The radiation dose rate value and the radiation dose, which are present in point B are again higher than the radiation dose rate value and the radiation dose, which are present in point C.

Figure 2:
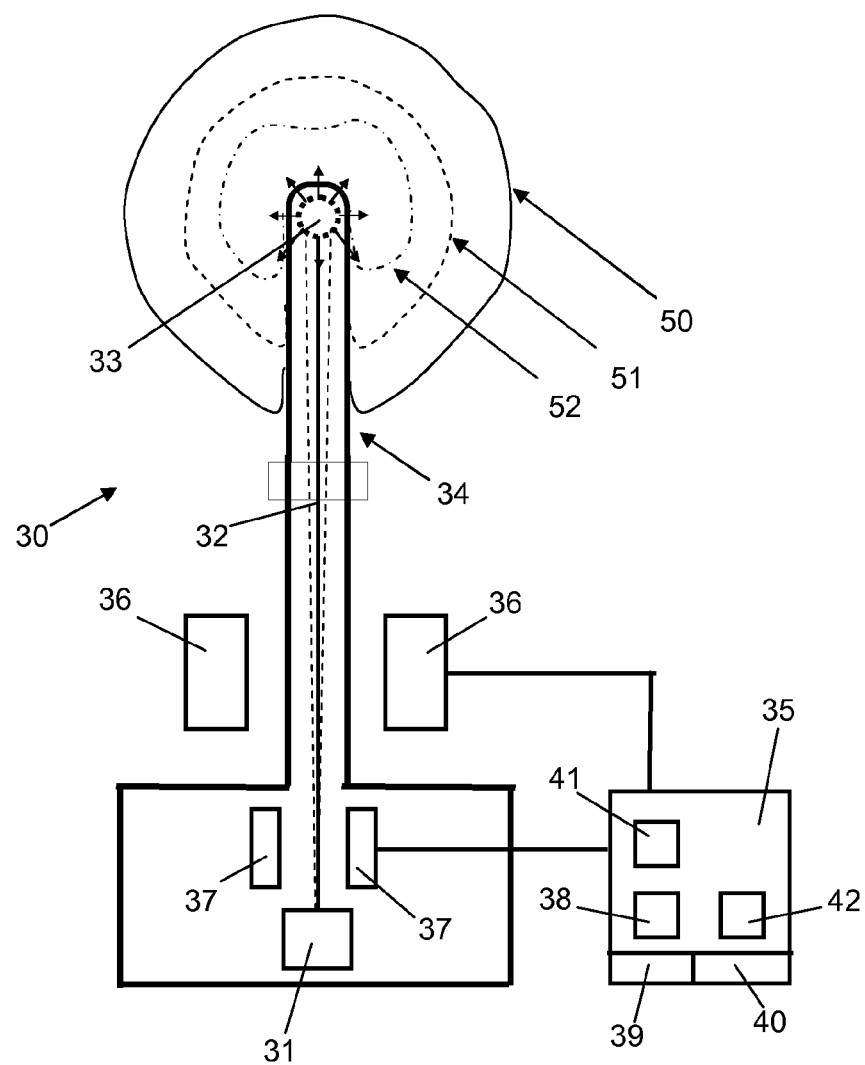
FIG. 2 shows a depiction of an apparatus for generating X-ray radiation.

The generating of the X-ray radiation can be performed by means of an apparatus 30, which is shown in FIG. 2. The apparatus 30 is in particular used in the field of intraoperative irradiation.

The apparatus 30 firstly has an electron source 31. By means of the electron source 31 electrons are generated, which in particular are emitted as an electron beam 32. The electron source 31 thus in particular serves for generating an electron beam 32. Furthermore, the apparatus has a target 33, wherein the target 33 may for example be made of gold. The target 33 serves for the actual generation of the X-ray radiation and/or X-ray radiation field, which is indicated by the arrows starting at the target 33. The target 33 is arranged in an evacuated tube 14 of an X-ray probe at its distal end.

The electrons, which are generated by the electron source 31, impinge on the target 33 as an electron beam 32. There, the electrons of the electron beam 32 are slowed down, whereby the X-ray radiation is generated, which is emitted from the target 33 with specific radiation characteristics, in particular with a specific radiation dose rate curve.

Furthermore, the apparatus 30 has a computing appliance 35. By means of this computing appliance 35 it becomes possible to influence the X-ray radiation.

Furthermore, it is provided, that the apparatus 30 has a deflection appliance 36 for deflecting the electron beam 32. The deflection appliance 36 may, for example, be magnetic deflection coils. By means of the deflection appliance 36, a magnetic field can be created, in order to deflect the electrons of the electron beam 32, which are accelerated towards the target 33, which is indicated by the dashed lines of the electron beam. This allows for setting the location, where the electrons impinge on the target 33. Thereby, in particular the spatial radiation profile of the generated and emitted X-ray radiation can be adjusted. By means of the deflection appliance 36, the electron beam 32 can be moved over and on the target 33.

In addition, the apparatus 30 has an acceleration appliance 37 for accelerating the electrons by means of an applied acceleration voltage, in particular a high voltage. The computing appliance 35 is designed for actuating the acceleration appliance 37, which is depicted in FIG. 2 by the corresponding connecting line. This means, that the computing appliance 35 is designed to handle the acceleration appliance 37 in such a way, that via the acceleration appliance 37 a desired acceleration voltage is provided. The actuation of the acceleration appliance 37 via the computing appliance 35 is effected such, that by actuating the acceleration appliance 37 the acceleration voltage for accelerating the electron beam 32, which impinges on the target 33, is varied. By means of the computing appliance 35 it can be provided, that the acceleration voltages are switched during the irradiation between at least two different acceleration voltage values. For this purpose, the acceleration appliance 37 is correspondingly actuated, for example controlled, via the computing appliance 35.

The computing appliance 35 may, as described in connection with the other figures, be used for determining and/or calculating the specific radiation dose rate curve from the predetermined radiation dose rate curves or for determining and/or calculating the X-ray radiation with specific radiation characteristics, in particular with the specific radiation dose rate curve, from the specification X-ray radiations with the defined radiation characteristics, in particular the predetermined radiation dose rate curves.

Generated or calculated radiation dose rate curves or parameters and/or values of the X-ray radiation with the specific radiation characteristics, in particular with the specific radiation dose rate curve, can be stored in a storage appliance 38. The storage appliance 38 can be allocated with or included in the computing appliance 35.

Furthermore, the computing appliance 35 may have an interface 39 and an input appliance 40, in order to be able to receive or input the required specification values, which are necessary for conducting the invention.

In a generating appliance 41, which is preferably part of the computing appliance 35, a specific radiation dose rate curve, or an X-ray radiation with specific radiation characteristics, in particular with a specific radiation dose rate curve can be generated from specification values.

By means of a time switching appliance 42, which is preferably part of the computing appliance 35, an irradiation, which is based on the generated and/or provided results, can be preformed in a subsequent manner or in a change.

The apparatus 30 is used to generate and/or provide an X-ray radiation field 50, 51, 52, so that a substrate 1, for example a tissue (not shown), can be irradiated.

A user, who wants to irradiate the substrate 1 from FIG. 1, wherein precisely put, the location 2, which is to be irradiated, of the substrate is to be irradiated, determines beforehand the radiation doses, which are to have been applied at points A, B and C after the irradiation time.

Figure 3:
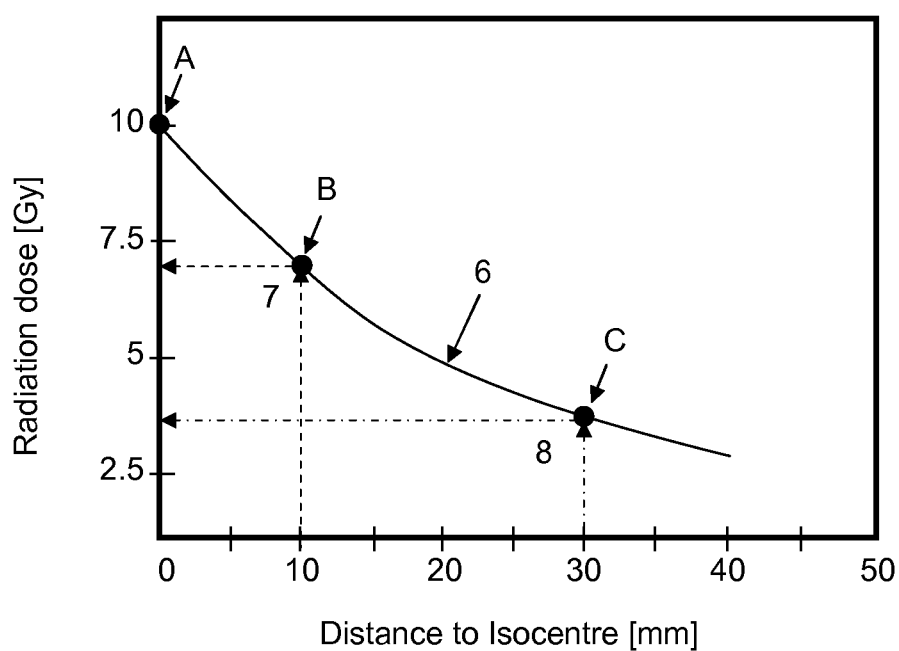
FIG. 3 shows a diagram of an exemplary radiation dose rate curve for the irradiation of a substrate.

This determination may for example be carried out with the diagram shown in FIG. 3. In FIG. 3 a diagram with an exemplary radiation dose rate curve for the irradiation of a substrate 1 is shown. On the y-axis the radiation dose in the physical unit Gray [Gy] and on the x-axis the distance to the isocentre in the physical unit millimeter [mm] is given.

As can be derived from the diagram in FIG. 3, at point A a radiation dose of ten Gray shall be applied, taking into account FIG. 1. At point B a radiation dose of seven Gray is thus to be applied at point B. At point C a radiation dose of 3.5 Gray is to be applied. The radiation doses of the different points, for example B and C can be determined by the arrows 7 and 8.

As can further be derived from FIG. 3, where the radiation dose is plotted over the distance from the isocentre, point A in accordance with FIG. 1 is at the surface of the substrate 1, that means immediately at the radiation source 3. Point B is corresponding to FIG. 1 between points A and C in a depth of ten millimeters within the substrate 1. Point C, which corresponds to the location 2, which is to be irradiated from FIG. 1, is in a depth of thirty millimeters underneath the surface of the substrate 1, that means within the substrate 1.

Due to the fixed radiation doses for points A, B and C a radiation dose curve 6 can be generated. By means of this radiation dose curve 6 for example also the radiation dose for a further point (not shown) can be determined.

The generating of a curve by connecting different points can be performed for different radiation doses and for different radiation dose rates. In the first case, a radiation dose curve is formed. In the second case a radiation dose rate curve is formed, which is shown in FIG. 4 in triplicate.

Figure 4:
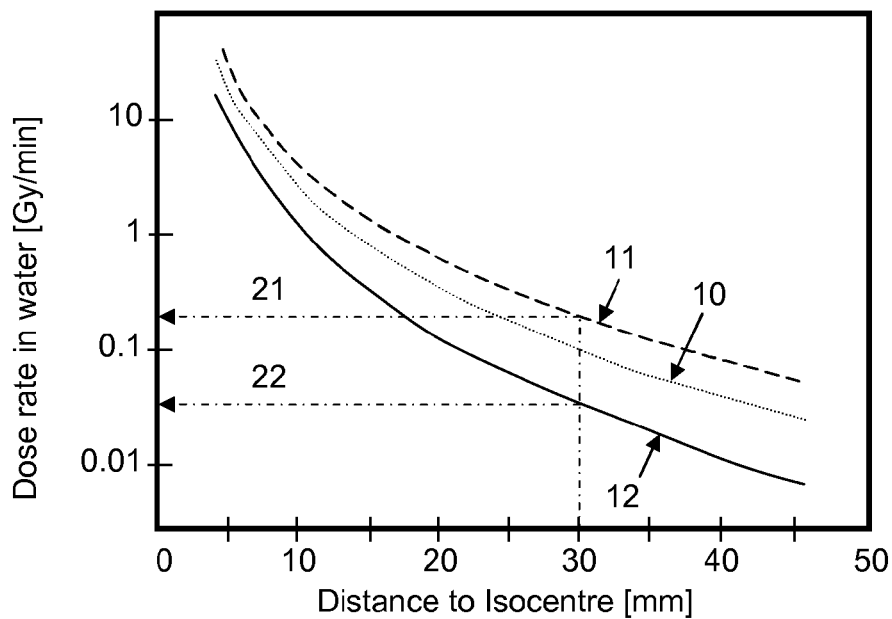
FIG. 4 shows a diagram of exemplary depth dose rate curves in water.

In FIG. 4 a diagram of exemplary depth dose rate curves in water 10, 11, 12, which hereinafter are also referred to as radiation dose rate curves, is shown. The depth dose rate curves in water are composed, as already described with respect to FIG. 3, of several distance dependent radiation dose rate values.

In FIG. 4, the values of the depth dose rate in water or the radiation dose rate curve against the distance from the isocentre of the radiation source 3 are shown.

The depth dose rate in water is the radiation dose rate, which has to be applied for the irradiation time on a substrate, in order to generate or apply a defined radiation dose. The irradiation time can also be referred to as the irradiation time frame, duration or treatment time, time frame or duration. Simply put, a radiation dose can be generated by the product of radiation dose rate and irradiation time.

The physical unit of the radiation dose rate and/or depth dose rate in water is given in Gray per minute [Gy/min]. The depth dose rate in water shown in FIG. 4 is given on the y-axis. The plotting in general is performed logarithmic. On the x-axis of the diagram of FIG. 4, the distance towards the isocentre is shown. The distance is given in the physical unit millimeter [mm].

The radiation which is emitted from the radiation source 3, is the highest immediately after the location of the emission, which is for example derivable in FIG. 4 from the fact, that the radiation dose rate curve at a small distance to the isocentre 3 has the highest values.

In FIG. 4 overall three curves 10, 11, 12 are shown. The three curves 10, 11, 12 are a specific radiation dose rate curve 10 and two predetermined radiation dose rate curves 11, 12. The course of the predetermined radiation dose rate curves 11, 12 is generated by respective application of an acceleration voltage at the radiation source 3.

By applying an acceleration voltage at the radiation source 3, the X-ray radiation, which is higher in immediate vicinity to the radiation source 3 than in a distance thereto, is generated from the radiation source 3 and emitted. The generating of the X-ray radiation can for example be derived from FIG. 2. Simply put, it can be said, that the intensity of the radiation or the radiation decreases with increasing distance to the radiation source 3 or to the isocentre. This behavior is also shown in the three radiation dose rate curves 10, 11, 12, which are shown in FIG. 4.

If substrate, for example tissue, is to be irradiated with a defined radiation, the location, at which the radiation is to arrive, is of crucial importance. This is the case, as the radiation source 3, as shown in FIG. 1, can normally not be guided directly to or into the location 2, which is to be irradiated, so that a distance between the location 2, which is to be irradiated, and the radiation source 3 exists.

As shown in FIG. 1 and in FIG. 3, a radiation dose of 3.5 Gray is to be applied, for irradiating the location 2, which is to be irradiated, at point C, which is in thirty millimeters depth from the surface of the substrate 1. By using FIG. 4, it can in general be determined under consideration of the predetermined radiation dose rate curves 11, 12, which conditions, that means which radiation dose rate curve values and irradiation time is necessary for that.

As already described above, a predetermined radiation dose rate curve 11, 12 is generated by applying an acceleration voltage. That means that a specific acceleration voltage leads to a characteristic radiation dose rate curve 11, 12. A different acceleration voltage, in contrast, leads to a different radiation dose rate curve 11, 12. For example, the predetermined radiation dose rate curves 11, 12 shown in FIG. 4 can be generated by applying two different acceleration voltages.

For example, an X-ray radiation can be generated, where an electron beam is accelerated with an acceleration voltage of fifty kilovolt. Due to this acceleration voltage, for example, radiation dose rate curve 11 can be formed. By applying an AC of for example thirty kilovolts, for example the radiation dose rate curve 12 can be formed.

If at point C of FIG. 1, as an example, in thirty millimeter depth, a required radiation dose of 3.5 Gray is to be applied; this may for example either be achieved by using the predetermined radiation dose rate curve 11 or the predetermined radiation dose rate curve 12.

If for example two acceleration voltages can be applied, the radiation dose rate curves 11 and 12 can be achieved.

As can be derived from FIG. 4, by using the predetermined radiation dose rate curve 11 or 12 in thirty millimeter depth from the surface of the substrate 1 (point C), a radiation dose rate value of 0.2 Gray per minute (predetermined radiation dose rate curve 11) or 0.05 Gray per minute (predetermined radiation dose rate curve 12), is applied, which is obvious from arrows 21 and 22.

In order to apply the required radiation dose of 3.5 Gray at point C, the irradiation would have to last 17.5 minutes when using radiation dose rate curve 11 and 70 minutes when using radiation dose rate curve 12.

As can be derived from FIG. 3, it is set by the user, that at point A and point B also defined radiation doses are to be applied. Hence, at all three points (A, B, C) defined radiation doses are to be applied, which is not possible with the predetermined radiation dose rate curve 11 or the predetermined radiation dose rate curve 12 by itself. If three radiation doses at points A, B, C by using the radiation dose rate curve 11 are for example to be applied, it may be, that with a irradiation time of 17.5 minutes, which is necessary for point C, at point A a radiation dose of more than ten Gray and at point B a radiation dose of more than seven Gray is applied. Such a result is however not acceptable for the user. The same statement may be made for radiation dose rate curve 12.

It may, however, also be, that the required radiation dose for points A, B, C can be applied by the specific radiation dose rate curve 10. Furthermore, it may be that the radiation dose rate curve 10 is achieved by an acceleration voltage of 40 kV, for which however, so far no measuring values are available. Under such conditions, an irradiation using the method according to the invention is possible.

As already explained, the required radiation doses could be achieved as a radiation dose curve by the radiation dose rate values in form of the specific radiation dose rate curve 10. Therein, the overall irradiation time may for example be calculated to be 10 minutes. That means, that during an irradiation of the substrate using a radiation, which is achieved by applying an acceleration voltage of 40 kV, in or at all three points A, B, C after the irradiation time of 10 minutes, the required radiation dose has been applied.

This can be carried out, as described above, by proportional usage of two or more predetermined radiation dose rate curves 11, 12. In the example shown in FIG. 4, the suitable, that means specific, radiation dose rate curve 10 lies between the predetermined radiation dose rate curves 11, 12.

When using the method according to the present invention, the specific radiation dose rate curve 10 is generated by proportional composing of the predetermined radiation dose rate curves 11, 12. This is for example carried out by suitable control algorithms.

The adaption can be preformed by, for example, determining for a distance or several distances from the isocentre the defined radiation dose rate values. This can be set by the user directly or by means of a computing program. These determined radiation dose rate values then result, for example, in the specific radiation dose rate curve 10.

In such a case, the required specific radiation dose rate curve 10 can be formed by the predetermined radiation dose rate curves 11, 12, by proportionally using the radiation dose rate values of the predetermined radiation dose rate curve 11, 12, which are available, for the corresponding distances, that means same distances, from the isocentre of the radiation source 3.

For a better understanding this will now be described again by means of an example. At point C, which is thirty millimeters underneath the surface of the substrate 1, a radiation dose of 3.5 Gray is to be applied. This can, for example, be achieved by adapting the irradiation time by the two radiation dose rate curves 11, 12, which are available, that means the predetermined radiation dose rate curves 11, 12. If, however, at point B, in ten millimeters depth from the surface of the substrate 1, a radiation dose of seven Gray is to be applied, the required radiation dose at point B cannot be achieved, when using the irradiation time for point C.

It may, however, be, that by a proportional combination of the predetermined radiation dose rate curves 11, 12 at points B and C, the required radiation dose can be applied. Taking into consideration the irradiation time, which may, for example, be set to be ten minutes, the required radiation doses at/in points B and C can for example be applied by using from the predetermined (first) radiation dose rate curve 11 0.69 parts or portions and from the predetermined (second) radiation dose rate curve 12 0.31 parts or portions. The determination of the parts can, as already described above, be performed by control algorithms. In that case, it is provided, that the acceleration voltages are switched in a corresponding way. In order to achieve the proportional adaption, it is necessary, that different acceleration voltages can be applied alternately to the radiation source 3. Therein the change(s) or switching(s) may for be freely chosen. This adaption may, as already explained, for example be carried out by means of a computer program or a simulation program.

As the predetermined radiation dose rate curve 11, 12 or the radiation dose rate values at the points B and C cannot be changed, when using the predetermined radiation dose rate curves 11, 12, the determined portions have an influence on the resulting irradiation time. With respect to the above mentioned example, where the irradiation time is supposed to be ten minutes, it would result in, that the irradiation time, when using the predetermined (first) radiation dose rate curve 11, would result in 0.69 times 10 minutes and the irradiation time, when using the predetermined (second) radiation dose rate curve 12, would result in 0.31 times ten minutes.

Figure 5:
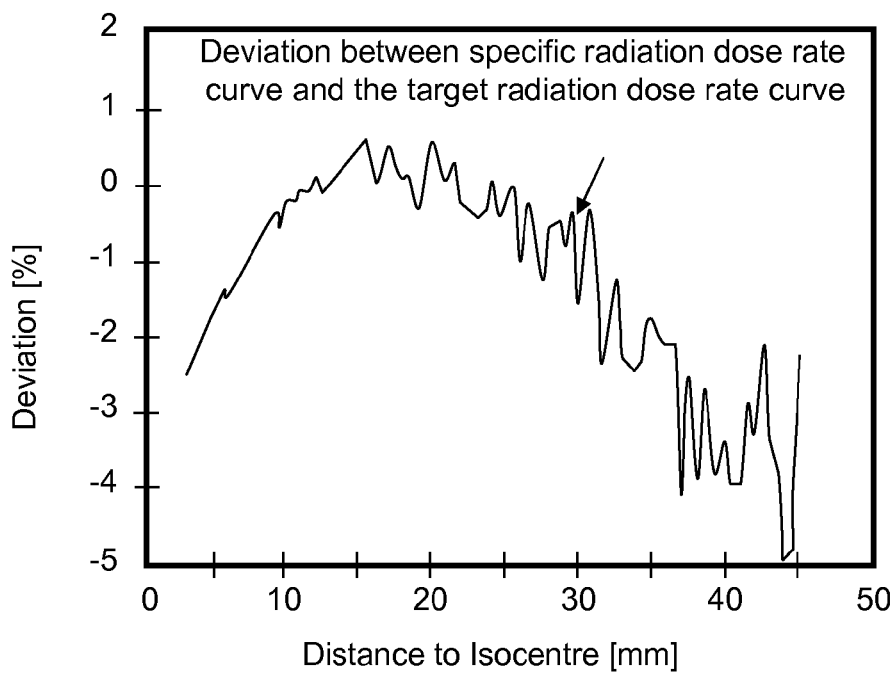
FIG. 5 shows a diagram of deviations between a defined radiation dose rate curve and a target radiation dose rate curve.

In FIG. 5 a diagram is shown, wherein the deviation between a specific radiation dose rate curve 10, which is proportionally composed by two predetermined radiation dose rate curves 11, 12 and a target radiation dose rate curve is depicted.

On the y-axis of the diagram, the deviations are given in percent, which occur between the specific radiation dose rate values and the target radiation dose rate values. On the x-axis of the diagram, again the distance to the isocentre, that means the radiation source is given.

As can be derived from the diagram in FIG. 5, the generating of a specific radiation dose rate curve 10 by two or more predetermined radiation dose rate curves 11, 12 may be subject to errors, in that the target radiation dose rate curve is not perfectly approximated by the proportional composing of the at least two predetermined radiation dose rate curves 11, 12. This is caused by the fact, that by adapting the specific radiation dose rate curve 10, only an approximation to the target radiation dose rate curve is performed. The calculation of the specific radiation dose rate curve 10 is to be carried out as exactly as possible, so that the error is as low as possible, that means that the reality can be well reflected.

As can also be derived from the diagram in FIG. 5, the error between the adaption of the specific radiation dose rate curve 10, which has been proportionally composed by the two predetermined radiation dose rate curves 11, 12, and the target radiation dose rate curve, that means the measured or calculated radiation dose rate curve, is in the range of a few percent, in the present case in the range of one percent to minus five percent. The error is so low, that an adaption, even if subject to errors, can be considered to be sufficiently accurate. This is supported by the fact, that not all radiation sources 3, even when identical in design, generate the same radiation dose rate curves 11, 12.

Figure 6:
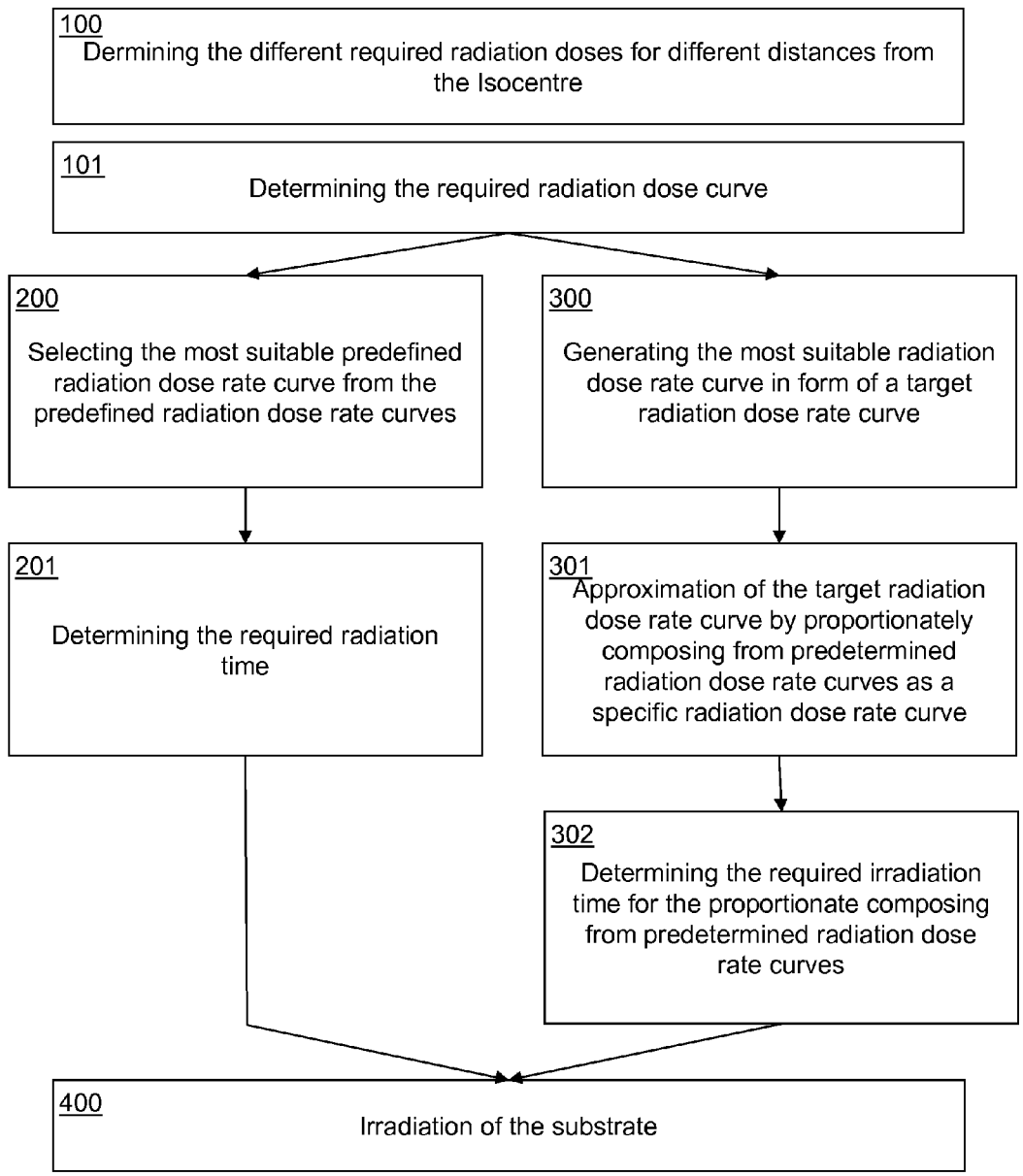
FIG. 6 shows a flowchart for irradiation a substrate.

In FIG. 6 two different approaches for irradiating a substrate 1 are shown.

The approaches shown in FIG. 6, which are given as a flow chart, in general refer to the examples from FIGS. 1, 3 and 4.

In order to irradiate a substrate 1 by means of a radiation source 3, the user determines the different required radiation doses for different distances from the isocentre (step 100) or they set these radiation doses. This is, for example, shown in FIG. 3.

In a further step 101, the required radiation dose curve is determined on the basis of the desired radiation doses.

With known irradiation of substrates 1, often only one radiation dose rate curve 11 or 12, that means only one predetermined radiation dose rate curve 11, 12, is available. If two predetermined radiation dose rate curves 11, 12 are available, the user chooses or selects the most suitable radiation dose rate curve 11 or 12 (DDC) from the predetermined radiation dose rate curves (step 200). Based on the selected predetermined radiation dose rate curve 11 or 12, the user determines the required irradiation time (step 201). Subsequently the irradiation of the substrate 1 is carried out (step 400).

With this approach, it may occur, that the radiation doses, which are desired and specified by the user, as a radiation dose curve are not reached, so that the substrate 1 is not irradiated as desired.

With the method according to the invention, it is possible to generate any specific radiation dose rate curve 10, that means also a random radiation dose curve by two or more predetermined radiation dose rate curves 11, 12.

In the beginning of the irradiation, with the method according to the invention, steps 100 and 101 are carried out corresponding to the above mentioned approach.

After determining the radiation dose curve (step 101), however, not one predetermined radiation dose rate curve 11, 12 is selected, but the most suitable radiation dose rate curve is generated as the target radiation dose rate curve (step 300).

If the target radiation dose rate curve can, however, not be generated by the radiation source 3 or if no survey has been carried out for this target radiation dose rate curve, in step 301 the approximation of the target radiation dose rate curve by proportional composing from predetermined radiation dose rate curves 11, 12 as the specific radiation dose rate curve 10 is performed.

In the further course (step 302) the required irradiation time(s) for the proportional composing from the predetermined radiation dose rate curves 11, 12 is determined.

As with the other approach, the irradiation of the substrate 1 is carried out after step 302 (step 400).

REFERENCE NUMBERS

A Point
B Point
C Point
1 Substrate (tissue)
2 Location which is to be irradiated (tumor)
3 Radiation source (isocentre)
4 Applicator
5 Radiation
6 Radiation dose curve
7 Determination of the radiation dose for point B
8 Determination of the radiation dose for point C
10 Determined radiation dose rate curve
11 Predetermined radiation dose rate curve (first)
12 Predetermined radiation dose rate curve (second)
21 Determination arrow
22 Determination arrow
30 Apparatus for generating X-ray radiation,
31 Electron source
32 Electron beam
33 Target
34 Tube of an X-ray probe
35 Computing device
36 Deflection appliance
37 Acceleration appliance
38 Storage appliance
39 Interface
40 Input appliance
41 Generating appliance
42 Time switch appliance
100 Flowchart step
101 Flowchart step
200 Flowchart step
201 Flowchart step
300 Flowchart step
301 Flowchart step
302 Flowchart step
400 Flowchart step

The invention claimed is:

1. Method for generating a specific radiation dose rate curve for an X-ray radiation for irradiation of a substrate, wherein the specific radiation dose rate curve represents a radiation dose rate as a function of distance, characterized in that the specific radiation dose rate curve is generated by selecting at least two predetermined radiation dose rate curves which are different from the specific radiation dose rate curve which is to be generated, and each of which represents a radiation dose rate as a function of distance, and by composing the specific radiation dose rate curve proportionally from the at least two predetermined radiation dose rate curves.

2. Method according to 1, characterized in that the specific radiation dose rate curve is determined from the predetermined radiation dose rate curves or that the specific radiation dose rate curve is determined from specification values for a specific radiation dose rate curve.

3. Method according to claim 1, characterized in that the generated radiation dose rate curve is stored in a storage appliance.

4. Method according to claim 1, characterized in that the specific radiation dose rate curve is composed from the at least two predetermined radiation dose rate curves by means of linear combination.

5. Method for generating X-ray radiation with a specific radiation dose rate curve, characterized in that the X-ray radiation is generated by proportionally composing the X-ray radiation with the specific radiation dose rate curve from a first specification X-ray radiation with a predetermined first radiation dose rate curve and a second specification X-ray radiation with a predetermined second radiation dose rate curve, wherein the second specification X-ray radiation and wherein each of the specific dose rate curve, the predetermined first radiation dose rate curve, and the predetermined second radiation dose rate curve represents a radiation dose rate as a function of distance.

6. Method for generating X-ray radiation according to claim 2, wherein by means of an electron source an electron beam is generated, wherein the electron beam is directed accelerated by means of an acceleration voltage towards a target and wherein an X-ray radiation is generated by electrons of the electron beam impinging on the target, characterized in that the X-ray radiation is generated by proportionally composing the X-ray radiation with the specific radiation dose rate curve from a first specification X-ray radiation with the predetermined first radiation dose rate curve, which is associated to a first acceleration voltage, and a second specification X-ray radiation with the predetermined second dose rate curve, which is associated to a second acceleration voltage, wherein the second specification X-ray radiation differs from the first specification X-ray radiation, by proportionally and alternating accelerating the electron beam with the first acceleration voltage and with the second acceleration voltage.

7. Method according to claim 2, characterized in that the X-ray radiation with the specific radiation dose rate curve is determined from the specification X-ray radiations with the predetermined radiation dose rate curves or that the X-ray radiation with the specific radiation dose rate curve is determined from specification values for an X-ray radiation with a specific radiation dose rate curve.

8. Method according to claim 2, characterized in that parameters and/or values of the generated X-ray radiation with the specific radiation dose rate curve are stored in a storage appliance.

9. Method according to claim 2, characterized in that the X-ray radiation with the specific radiation dose rate curve is composed by means of linear combination from the first specification X-ray radiation and the second specification X-ray radiation.

10. Apparatus for generating a specific radiation dose rate curve for an X-ray radiation for irradiating a substrate, wherein the specific radiation dose rate curve represents a radiation dose rate as a function of distance, characterized in that the apparatus has a selection appliance for selecting at least two predetermined radiation dose rate curves, which are different from the specific radiation dose rate curve which is to be generated, each of which represents a radiation dose rate as a function of distance, and that the apparatus has an appliance for proportionally composing the specific radiation dose rate curve from the at least two predetermined radiation dose rate curves.

11. Apparatus according to claim 9, characterized in that the apparatus has a computing appliance for determining the specific radiation dose rate curve from the predetermined radiation dose rate curves and/or that the apparatus has a storage appliance for storing the specific radiation dose rate curve.

12. Apparatus according to claim 9, characterized in that the apparatus has an interface for receiving and/or an input appliance for input of specification values for a specific radiation dose rate curve and/or that the apparatus has a generating appliance for generating a specific radiation dose rate curve or an X-ray radiation.

13. Apparatus for generating X-ray radiation with a specific radiation dose rate curve characterized in that the apparatus has an appliance for providing a first specification X-ray radiation with a specified first radiation dose rate curve and a and wherein each of the specific dose rate curve, the predetermined first radiation dose rate curve, and the predetermined second radiation dose rate curve represents a radiation dose rate as a function of distance with a predetermined second radiation dose rate curve, wherein the second specification X-ray radiation is different from the first specification X-ray radiation, and that the apparatus has an appliance for proportionally composing the X-ray radiation with the specific radiation dose rate curve from the first specification X-ray radiation and the second specification X-ray radiation.

14. Apparatus for generating of X-ray radiation according to claim 10, characterized by an electron source for generating an electron beam, a target for generating X-ray radiation through electrons from the electron beam impinging on the target, an acceleration appliance for accelerating the electrons of the electron beam by means of an applied acceleration voltage, an appliance for providing a first specification X-ray radiation with a predetermined first radiation dose rate curve, which is associated to a first acceleration voltage and a second specification X-ray radiation, which is different from the first X-ray radiation, with a predetermined second radiation dose rate curve, which is associated to a second acceleration voltage, as well as an appliance for proportionally composing the X-ray with the specific radiation dose rate curve from the first specification X-ray radiation and the second specification X-ray radiation, wherein the appliance is designed for influencing the accelerating appliance, such that the electron beam is accelerated or can be accelerated proportionally alternately with the first acceleration voltage and the second acceleration voltage.

15. Apparatus according to claim 10, characterized in that it has means for carrying out a method for generating a specific radiation dose rate curve for an X-ray radiation for irradiation of a substrate, wherein the specific radiation dose rate curve represents a radiation dose rate as a function of distance, characterized in that the specific radiation dose rate curve is generated by selecting at least two predetermined radiation dose rate curves which are different from the specific radiation dose rate curve which is to be generated, and each of which represents a radiation dose rate as a function of distance, and by composing the specific radiation dose rate curve proportionally from the at least two predetermined radiation dose rate curves.

16. Apparatus according to claim 10, characterized in that the apparatus has a computing appliance for determining the X-ray radiation with the specific radiation dose rate curve from the specification X-ray radiations with the defined radiation dose rate curves and/or that the apparatus has a storage appliance for storing parameters and/or values of the X-ray radiation with the specific radiation dose rate curve.

17. Apparatus according to claim 10, characterized in that the apparatus has an interface for receiving and/or an input appliance for input of specification values for the X-ray radiation with the specific radiation dose rate and/or that the apparatus has a generating appliance for generating an X-ray radiation with a specific radiation dose rate curve from specification values.

18. Apparatus according to claim 11, characterized in that it has means for carrying out a method for generating X-ray radiation with a specific radiation dose rate curve, characterized in that the X-ray radiation is generated by proportionally composing the X-ray radiation with the specific radiation dose rate curve from a first specification X-ray radiation with a predetermined first radiation dose rate curve and a second specification X-ray radiation with a predetermined second radiation dose rate curve, wherein the second specification X-ray radiation differs from the first specification X-ray radiation.

19. Method for generating X-ray radiation with a specific radiation dose rate curve, characterized in that the X-ray radiation is generated by proportionally composing the X-ray radiation with the specific radiation dose rate curve from a first specification X-ray radiation with a known first radiation dose rate curve and a second specification X-ray radiation with a known second radiation dose rate curve, wherein the second specification X-ray radiation differs from the first specification X-ray radiation.

20. Apparatus for generating X-ray radiation with a specific radiation dose rate curve, characterized in that the apparatus has an appliance for providing a first specification X-ray radiation with a known first radiation dose rate curve and a second specification X-ray radiation with a known second radiation dose rate curve, wherein the second specification X-ray radiation is different from the first specification X-ray radiation, and that the apparatus has an appliance for proportionally composing the X-ray radiation with the specific radiation dose rate curve from the first specification X-ray radiation and the second specification X-ray radiation.

* * * * *